(12) United States Patent
Hattori et al.

(10) Patent No.: US 9,032,799 B2
(45) Date of Patent: May 19, 2015

(54) APPARATUS AND METHOD FOR NONDESTRUCTIVE INSPECTION

(75) Inventors: Hidetaka Hattori, Aichi (JP); Hideki Horizono, Aichi (JP); Masayuki Kanemasu, Aichi (JP); Shigeyuki Matsubara, Osaka (JP); Kunihiko Shinoda, Osaka (JP); Hirotoshi Hujigaki, Osaka (JP); Susumu Ryuuou, Osaka (JP)

(73) Assignee: MITSUBISHI HEAVY INDUSTRIES, LTD., Tokyo (JP)

( * ) Notice: Subject to any disclaimer, the term of this patent is extended or adjusted under 35 U.S.C. 154(b) by 581 days.

(21) Appl. No.: 13/128,948
(22) PCT Filed: Nov. 10, 2009
(86) PCT No.: PCT/JP2009/069099
§ 371 (c)(1), (2), (4) Date: Jul. 14, 2011
(87) PCT Pub. No.: WO2010/055823
PCT Pub. Date: May 20, 2010

(65) Prior Publication Data
US 2011/0259104 A1  Oct. 27, 2011

(30) Foreign Application Priority Data
Nov. 14, 2008 (JP) .................................. 2008-292743

(51) Int. Cl.
*G01N 29/032* (2006.01)
*G01N 29/04* (2006.01)

(52) U.S. Cl.
CPC ............ *G01N 29/032* (2013.01); *G01N 29/043* (2013.01); *G01N 2291/0231* (2013.01); *G01N 2291/0427* (2013.01)

(58) Field of Classification Search
CPC ............... G01N 29/02; G01N 29/043; G01N 2291/0231; G01N 2291/0427; G01N 2291/015; G01N 2291/022; G01N 2291/0228; G01N 2291/02416; G01N 2291/0251; G01N 2291/0422; G01N 2291/048; G01N 2291/102; G01N 29/024; G01N 29/032

USPC ............. 73/19.01, 19.03, 19.1, 53.01, 61.41, 73/61.79, 64.41, 64.42, 64.53, 599, 600, 73/624, 628, 641, 620, 622
See application file for complete search history.

(56) References Cited

U.S. PATENT DOCUMENTS 2,799,157 A * 7/1957 Pohlman ........................ 73/635
4,434,659 A * 3/1984 Kurtz et al. .................... 73/620
(Continued)

FOREIGN PATENT DOCUMENTS

EP  1 054 255  11/2000
JP  58-77655  5/1983
(Continued)

OTHER PUBLICATIONS

Chinese Office Action issued Dec. 18, 2012 in corresponding Chinese Patent Application No. 200980145460.0 with English translation.
(Continued)

*Primary Examiner* — Laura Martin
*Assistant Examiner* — Rose M Miller
(74) *Attorney, Agent, or Firm* — Wenderoth, Lind & Ponack, L.L.P.

(57) ABSTRACT

A nondestructive inspection apparatus according to the present invention has a transmission-side probe configured to emit a first ultrasonic wave toward a test-target fluid, a plate through which a Lamb wave generated by the first ultrasonic wave is propagated when the first ultrasonic wave is propagated, and a reception-side probe configured to measure intensity of a second ultrasonic wave which is emitted from the plate and propagates through the test-target fluid. At this time, the nondestructive inspection apparatus can inspect the test-target fluid without bringing the transmission-side probe configured to emit the first ultrasonic wave and the reception-side probe configured to measure the second ultrasonic wave into contact with the test-target fluid.

19 Claims, 5 Drawing Sheets

(56) References Cited

U.S. PATENT DOCUMENTS

| | | | |
|---|---|---|---|
| 4,452,080 A * | 6/1984 | McFarland | 73/588 |
| 4,494,408 A * | 1/1985 | DeLacy | 73/587 |
| H924 H * | 6/1991 | Chimenti | 73/644 |
| 5,058,432 A * | 10/1991 | Morkun et al. | 73/599 |
| 5,911,159 A * | 6/1999 | Choo et al. | 73/590 |
| 6,029,520 A * | 2/2000 | Beall et al. | 73/579 |
| 2002/0088281 A1 | 7/2002 | Gorman et al. | |
| 2003/0217599 A1 * | 11/2003 | Peterson et al. | 73/602 |
| 2008/0127731 A1 | 6/2008 | Shirai et al. | |
| 2011/0239769 A1 * | 10/2011 | Schmitt et al. | 73/632 |

FOREIGN PATENT DOCUMENTS

| | | |
|---|---|---|
| JP | 61-270656 | 11/1986 |
| JP | 7-311183 | 11/1995 |
| JP | 8-199988 | 8/1996 |
| JP | 2006-103190 | 4/2006 |
| JP | 2006-138818 | 6/2006 |
| JP | 3864180 | 12/2006 |
| JP | 2008-44358 | 2/2008 |
| SU | 930107 | 5/1982 |
| SU | 1015291 | 4/1983 |
| WO | 2008/034878 | 3/2008 |

OTHER PUBLICATIONS

Russian Decision of Grant of Patent for Invention issued Aug. 14, 2012 in corresponding Russian Patent Application No. 2011123776 with partial English translation.

English language Abstract of RU 2274856 having a publication date of Apr. 20, 2006.

Japanese Patent Office Action issued Feb. 13, 2013 in corresponding Japanese Patent Application No. 2008-292743 with partial English translation.

Decision to Grant a Patent, with English translation, issued Oct. 25, 2013 in corresponding Japanese Patent Application No. 2008-292743.

Chinese Decision to Grant a Patent issued Nov. 6, 2014 in corresponding Chinese Application No. 200980145460.0 with partial English translation.

International Search Report issued Dec. 8, 2009 in International (PCT) Application No. PCT/JP2009/069099.

* cited by examiner

APPARATUS AND METHOD FOR NONDESTRUCTIVE INSPECTION

TECHNICAL FIELD

The present invention relates to a nondestructive inspection apparatus and a nondestructive inspection method, and more particularly, relates to an apparatus and method for nondestructive inspection of a fluid with ultrasonic waves.

BACKGROUND ART

Fiber-reinforced composite material is known, which is reinforced by combining fiber with resin. The fiber-reinforced composite material is exemplified by CFRP (Carbon Fiber reinforced Plastics). Because such fiber-reinforced composite material has a great advantageous effect of light-weight, it is applied to many products such as an aircraft structural member. The fiber-reinforced composite material is manufactured by VaRTM (Vacuum assisted Resin Transfer Molding) and RFI (Resin Film Infusion), in which laminated reinforced fiber is impregnated in resin and then the resin is hardened. In the fiber-reinforced composite material, defects such as a void and failure of impregnation of resin are sometimes caused. It is desired that such defects should be detected before the resin is hardened.

Japanese Patent No. 3,864,180 discloses an ultrasonic testing method which can clearly detect a defect portion by a noncontact reflection method. In the ultrasonic testing method, an ultrasonic wave is transmitted from a probe provided on one side of a test object and a reflected wave is received by the probe. The probe has a transmitter and a receiver. The ultrasonic wave is transmitted and received through an air layer between the transmitter and the receiver, and the test object. Relative positions of the transmitter, the receiver, and the test object are set so that an aerial transmission time between the transmitter and the receiver is longer than a transmission time of the reflected wave.

US Patent Publication US 2002/0088281A discloses an inspection method for performing inspection with use of a Lamb wave.

CITED REFERENCES

[Patent Literature 1]: Japanese Patent No. 3864180
[Patent Literature 2]: US 2002/0088281A

SUMMARY OF THE INVENTION

An object of the present invention is to provide a nondestructive inspection apparatus and a nondestructive inspection method, for reducing contamination of environment where a fluid is tested.

Another object of the present invention is to provide a nondestructive inspection apparatus and a nondestructive inspection method, for detecting a position of a portion of a fluid in a given state.

Still another object of the present invention is to provide a nondestructive inspection apparatus and a nondestructive inspection method, for detecting a position of a portion of a fluid in a given state with higher precision.

Still another object of the present invention is to provide a nondestructive inspection apparatus and a nondestructive inspection method, for detecting timing at which a fluid is set to a given state, without mixing a foreign substance into the fluid.

Still another object of the present invention is to provide a nondestructive inspection apparatus and a nondestructive inspection method, for detecting a defect caused in material before a fluid is hardened when the material is manufactured by hardening the fluid.

A nondestructive inspection apparatus according to the present invention has a transmission-side probe configured to emit a first ultrasonic wave toward a test-target fluid, a plate which propagates a Lamb wave generated by the first ultrasonic wave when the first ultrasonic wave is propagated, and a reception-side probe configured to measure intensity of a second ultrasonic wave which is emitted from the plate and propagates through the test-target fluid. At this time, the nondestructive inspection apparatus can inspect the test-target fluid without bringing the transmission-side probe configured to emit the first ultrasonic wave and the reception-side probe configured to measure the second ultrasonic wave into contact with the test-target fluid.

It is preferable that the plate is formed as part of a mold in which the test-target fluid is injected.

It is preferable that the nondestructive inspection apparatus according to the present invention further includes a fixing member configured to fix the reception-side probe to the transmission-side probe.

The nondestructive inspection apparatus according to the present invention further includes a first driving unit configured to drive the transmission-side probe and the reception-side probe. At this time, the nondestructive inspection apparatus can detect a position where the test-target fluid is in a given state.

It is preferable that the nondestructive inspection apparatus according to the present invention further includes a second driving unit configured to change a direction of the reception-side probe with respect to the transmission-side probe.

The nondestructive inspection apparatus according to the present invention further includes a control unit. The control unit includes a scanning section configured to scan the transmission-side probe and the reception-side probe by arranging the transmission-side probe and the reception-side probe in a first direction using the second drive unit, and scan the transmission-side probe and the reception-side probe by arranging the transmission-side probe and the reception-side probe in a second direction different from the first direction using the second drive unit. The control unit further includes collecting section configured to collect intensity of the second ultrasonic wave from the reception-side probe while the transmission-side probe and the reception-side probe are scanned, and a defect detecting section configured to detect a position where the test-target fluid is not appropriate, based on the intensity. At this time, the nondestructive inspection apparatus can detect a position where the test-target fluid is with higher precision.

It is preferable that the nondestructive inspection apparatus according to the present invention further includes a control unit configured to detect timing at which the test-target fluid is set to a given state, based on intensity of the second ultrasonic wave.

A nondestructive inspection method according to the present invention includes emitting a first ultrasonic wave toward a test-target fluid, the first ultrasonic wave being propagated to a plate through the test-target fluid, measuring intensity of a second ultrasonic wave which is propagated through the test-target fluid, and testing the test-target fluid based on the intensity. The nondestructive inspection method can test the test-target fluid without bringing the transmission-side probe configured to emit the first ultrasonic wave and the reception-side probe configured to measure the second ultrasonic wave, into contact with the test-target fluid.

The nondestructive inspection method according to the present invention further includes scanning the transmission-side probe, which emits the first ultrasonic wave, and the reception-side probe, which measures the intensity. The nondestructive inspection method can detect a position where the test-target fluid is not appropriate, based on the second ultrasonic wave.

The scanning step includes scanning the transmission-side probe and the reception-side probe in a state that the transmission-side probe and the reception-side probe are arranged in a first direction, and scanning the transmission-side probe and the reception-side probe in a state that the transmission-side probe and the reception-side probe are arranged in a second direction different from the first direction. The nondestructive inspection method can detect a position where the test-target fluid is not appropriate, based on the second ultrasonic wave with higher precision.

It is preferable that a composite material manufacturing method according to the present invention includes performing the nondestructive inspection method according to the present invention, and performing a next process when the test-target fluid is appropriate.

The nondestructive inspection apparatus and the nondestructive inspection method according to the present invention can inspect a test-target fluid without bringing the transmission-side probe for emitting an ultrasonic wave and the reception-side probe for measuring an ultrasonic wave, into contact with the test-target fluid.

DESCRIPTION OF EMBODIMENTS

Hereinafter, a nondestructive inspection apparatus according to the present invention will be described with reference to the attached drawings.

Figure 1:
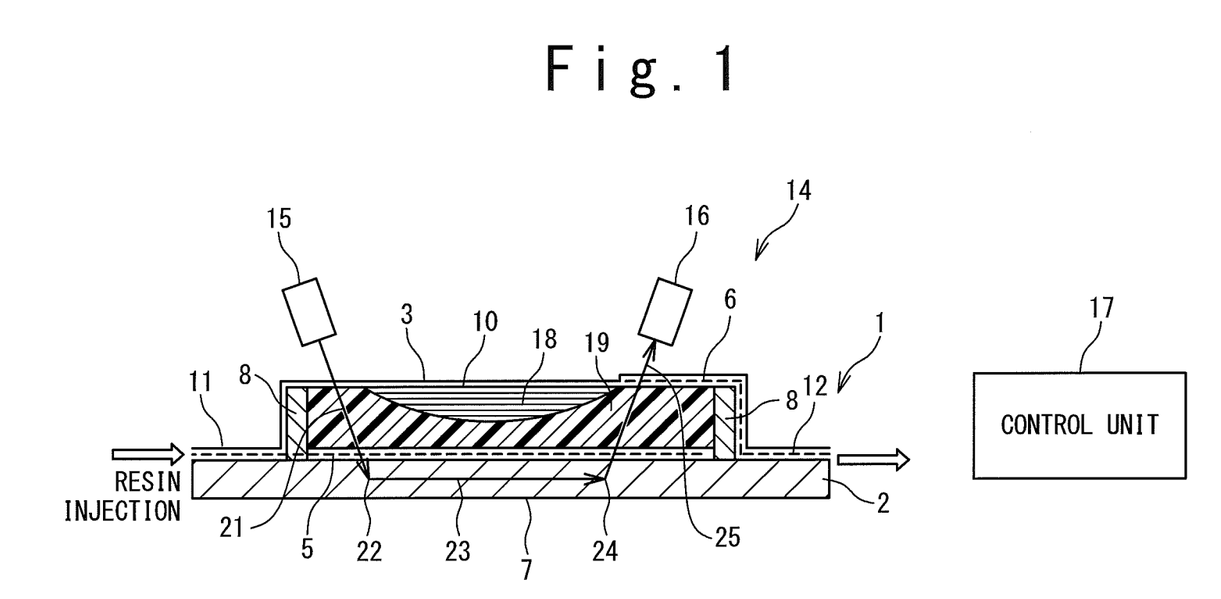
FIG. 1 is a block diagram showing a nondestructive inspection apparatus.

The nondestructive inspection apparatus is applied to a composite material curing tool. As shown in FIG. 1, a composite material curing tool 1 has a mold 2, a bag film 3, an injection-side resin distribution media 5, and a discharge-side resin distribution media 6. The mold 2 is made of material such as metal or CFRP, and is configured from a plate portion 7 and a sidewall portion 8. The plate portion 7 is formed in the form of a plate with a uniform thickness, and is formed to have a desired shape. The sidewall portion 8 is formed to project from the plate portion 7 into one direction. That is to say, the mold 2 is formed as a container with the plate portion 7 as a bottom and the sidewall portion 8 as a sidewall. A fiber-reinforced plastic intermediate material 10 is placed in the container of the mold 2. The fiber-reinforced plastic intermediate material 10 includes a fiber portion 18 and a resin portion 19. The fiber portion 18 is formed as laminated textiles made of carbon fiber. It should be noted that the fiber portion 18 may be made of fiber different from the carbon fiber. The fiber is exemplified by glass fiber. The resin portion 19 is made of epoxy resin, which is a fluid, and the fiber portion 18 is impregnated therein. The resin portion 19 is heated and hardened so that the fiber-reinforced plastic intermediate material 10 changes to fiber-reinforced plastic. It should be noted that that the resin portion 19 may be made of another thermosetting synthetic resin hardened through heating.

The bag film 3 covers the sidewall portion 8 over an above portion of the plate portion 7, to seal a container portion of the mold 2 from the outside. The bag film 3 further has an injection-port 11 and a vacuum-port 12. The injection-port 11 is disposed to connect a resin injecting unit (not shown) and the container portion of the mold 2. The resin injecting unit injects resin for the resin portion 19, into the container portion of the mold 2 through the injection-port 11. The vacuum-port 12 is disposed to connect a resin sucking unit (not shown) and the container portion of the mold 2. The resin sucking unit evacuates the container portion of the mold 2 through the vacuum-port 12, and sucks resin of the resin portion 19 to the outside of the mold 2.

The injection-side resin distribution media 5 is formed in the form of a net and is arranged to connect the injection-port 11 and the container portion of the mold 2. The injection-side resin distribution media 5 assists the resin to be injected from the resin injecting unit into the container portion of the mold 2. The discharge-side resin distribution media 6 is formed in the form of a net and is arranged to connect the vacuum-port 12 and the container portion of the mold 2. The discharge-side resin distribution media 6 assists the resin to be sucked from the container portion of the mold 2 to the resin sucking unit.

FIG. 1 further shows a nondestructive inspection apparatus. A nondestructive inspection apparatus 14 has a transmission-side probe 15, a reception-side probe 16, and a control unit 17. The control unit 17, which is a computer, has a CPU, a storage unit, an input unit, an output unit, and an interface, which are not shown. The CPU executes a computer program installed in the control unit 17, and controls the storage unit, the input unit, the output unit, and the interface. The storage unit stores the computer program, and temporarily stores data generated by the CPU. The input unit generates data through an operation by a user, and outputs the data to the CPU. The input unit is exemplified by a keyboard. The output unit outputs data generated by the CPU so that the user can recognize the data. The output unit is exemplified by a display. The interface outputs to the CPU, data generated by an external unit connected to the control unit 17, and outputs data generated by the CPU to the external unit. The external unit includes the transmission-side probe 15 and the reception-side probe 16.

The transmission-side probe 15 is arranged to face the bag film 3 of the composite material curing tool 1. The transmission-side probe 15 is connected to the control unit 17 through an electric wire (not shown), to allow data to be transmitted. The transmission-side probe 15 is controlled by the control unit 17, and emits an ultrasonic wave 21 toward the plate portion 7 of the mold 2. The ultrasonic wave 21 is propagated to the plate portion 7 of the mold 2 through the fiber-reinforced plastic intermediate material 10 in the container portion of the mold 2. A Lamb wave 23 is generated at a point 22 of the plate portion 7, to which the ultrasonic wave 21 is propagated, and the plate portion 7 propagates the Lamb wave 23. The reception-side probe 16 is arranged to face the bag film 3 of the composite material curing tool 1 and be directed to a point 24 of the plate portion 7. The point 24 is set to a position away from the point 22 by a given distance. The reception-side probe 16 is connected to the control unit 17 through an electric wire (not shown), so that data can be transmitted. The reception-side probe 16 receives an ultrasonic wave 25 which is emitted from the point 24 and propagated through the fiber-reinforced plastic intermediate material 10 in the inside of the mold 2. Intensity of the ultrasonic wave 25 represents the thickness of the portion 19, through which the ultrasonic wave 21 is propagated, of the fiber-reinforced plastic intermediate material 10, and the thickness of the resin portion 19, through which the ultrasonic wave 25 is propagated, of the fiber-reinforced plastic intermediate material 10. The reception-side probe 16 measures intensity of the ultrasonic wave 25 and outputs the intensity to the control unit 17.

Figure 2:
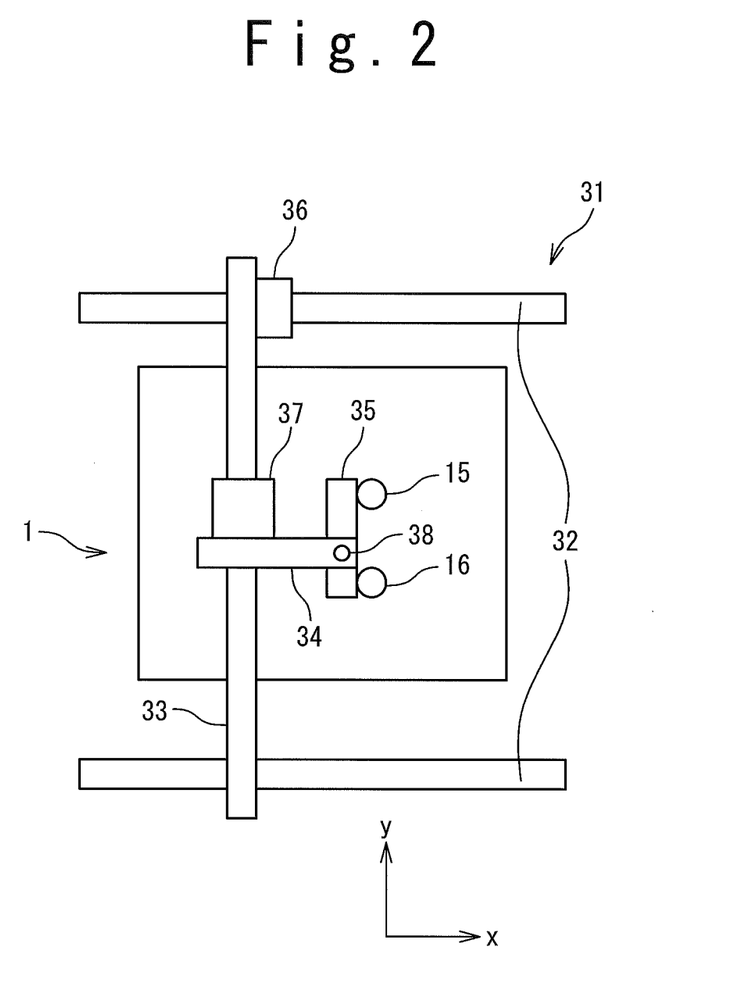
FIG. 2 is a plan view showing the nondestructive inspection apparatus.

As shown in FIG. 2, the nondestructive inspection apparatus 14 further has a scanner 31. The scanner 31 has guide rails 32, a first supporting member 33, a second supporting member 34, and a fixing member 35. The guide rails 32 are made in the shape of rods, and fixed to a base on which the mold 2 of the composite material curing tool 1 is fixed, so that the guide rails 32 are positioned in parallel to the x-axis direction. The first supporting member 33 is made in the shape of a rod and positioned in parallel to the y-axis direction perpendicular to the x-axis direction. The first supporting member 33 is supported by the guide rails 32 so that the first supporting member 33 can move in a direction parallel to the x-axis direction. The second supporting member 34 is made in the shape of a rod and positioned in parallel to the x-axis direction perpendicular to the y-axis direction. The second supporting member 34 is supported by the first supporting member 33 so that the second supporting member 34 can move in a direction parallel to the y-axis direction. The fixing member 35 is made in the shape of a rod and supported by the second supporting member 34 so that the fixing member 35 can rotate around an axis parallel to a vertical direction perpendicular to the x-axis direction and the y-axis direction.

The scanner 31 further has a first driving unit 36, a second driving unit 37, and a third driving unit 38. The first driving unit 36, the second driving unit 37, and the third driving unit 38 are connected to the control unit 17 through electric wires which are not shown, so that data can be transmitted. The first driving unit 36 is controlled by the control unit 17 to drive the first supporting member 33 so that the first supporting member 33 moves in a direction parallel to the x-direction with respect to the guide rails 32. The second driving unit 37 is controlled by the control unit 17 to drive the second supporting member 34 so that the second supporting member 34 moves in a direction parallel to the y-axis direction with respect to the first supporting member 33. The third driving unit 38 is controlled by the control unit 17 to drive the fixing member 35 so that the fixing member 35 rotationally moves around an axis parallel to a vertical direction with respect to the second supporting member 34.

According to the scanner 31, when the transmission-side prove 15 is directed toward the point 22 of the plate portion 7, the reception-side prove 16 is directed at the point 24 at all times, which is away from the point 22 by a given distance, and can measure intensity of the ultrasonic wave 25 emitted from the point 24.

Figure 3:
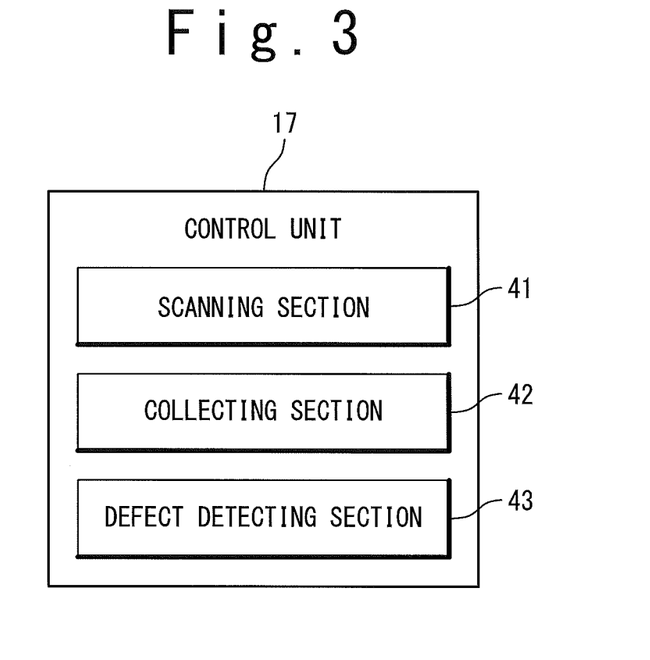
FIG. 3 is a block diagram showing a control unit.

As shown in FIG. 3, a plurality of computer programs are installed in the control unit 17. The computer programs include a scanning section 41, a collecting section 42, and a defect detecting section 43.

The scanning section 41 drives the third driving unit 38 so that the transmission-side probe 15 and the reception-side probe 16 are arranged in either the x-axis direction or the y-axis direction. The scanning section 41 controls the first driving unit 36 and the second driving unit 37 in a state that the transmission-side probe 15 and the reception-side probe 16 are arranged to direct either the x-axis direction or the y-axis direction, to scan the transmission-side probe 15 and the reception side probe 16. That is to say, a part surrounded by the sidewall portion 8 corresponding to the plate portion 7 is divided into a plurality of regions in a matrix pattern. The scanning section 41 controls the first driving unit 36 and the second driving unit 37 so that the transmission-side probe 15 is directed toward each of the regions in order.

The collecting section 42 emits the ultrasonic wave 21 by using the transmission-side probe 15 each time the transmission-side probe 15 is directed toward each of the regions by the scanning section 41. The collecting section 42 measures intensity of the ultrasonic wave 25 emitted from the plate portion 7 by using the reception-side probe 16 each time the ultrasonic wave 21 is emitted from the transmission-side probe 15, and the intensities of the ultrasonic wave 25 are collected from the reception-side probe 16.

The defect detecting section 43 determines whether or not any defect is caused in the fiber-reinforced plastic intermediate material 10 based on the intensities of the ultrasonic wave 25 collected by the collecting section 42. When determining that the defect is caused in the fiber-reinforced plastic intermediate material 10, the defect detecting section 43 calculates a position, type, and size of the defect, based on the collected intensities of the ultrasonic wave 25. The defect detecting section 43 further displays the calculated position, type, and size of the defect on the display so that the user can recognize the calculated position, type, and size of the defect.

Figure 4:
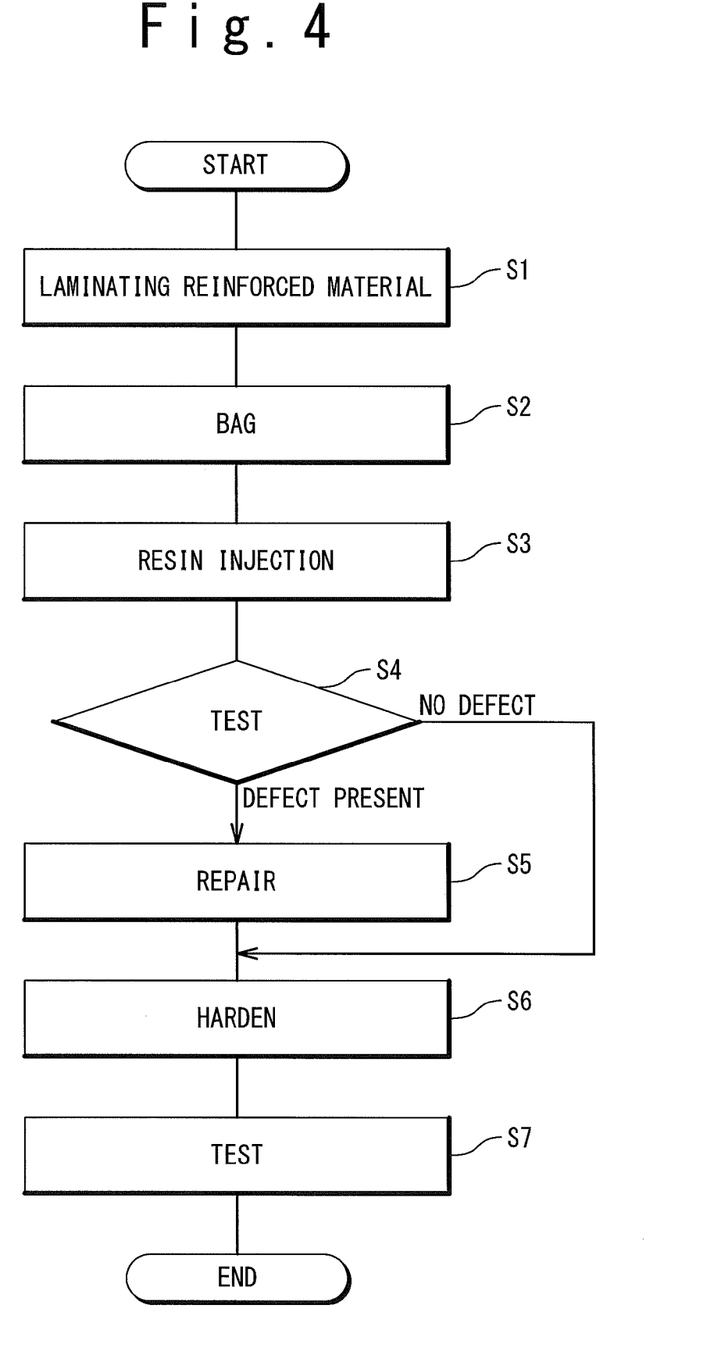
FIG. 4 is a flow chart showing a composite material manufacturing method.

A nondestructive inspection method according to an embodiment of the present invention is applied to a composite material manufacturing method. FIG. 4 shows the composite material manufacturing method. A user firstly laminates a plurality of sheets made of carbon fiber and arranges the laminated sheets in the container portion of the mold 2 (step S1). Next, the user arranges the injection-side resin distribution media 5 and the discharge-side resin distribution media 6 in the container portion of the mold 2, and seals the container portion of the mold 2 from the outside by using the bag film 3 (step S2). Then, the user forms the injection-port 11 and the vacuum-port 12, and connects the injection-port 11 and the vacuum-port 12 to the resin injecting unit and the resin sucking unit, respectively. Thus, the composite material curing tool 1 is completed.

Moreover, the user places the composite material curing tool 1 in a furnace, and installs the nondestructive inspection apparatus 14 to the composite material curing tool 1. While heating the composite material curing tool 1 to a temperature of in a range of 70° C. to 80° C. by using the furnace, the user evacuates the container portion of the mold 2 by using the resin sucking unit and then injects resin into the container portion of the mold 2 by using the resin injecting unit. After the resin reaches the vacuum-port 12, the user discharges the resin outside the mold 2 by using the resin sucking unit (step S3). The laminated sheets are formed into the fiber-reinforced plastic intermediate material 10 as a result of such injection of resin.

While injecting the resin in the container portion of the mold 2, the user performs the nondestructive inspection method, to determine whether or not any defect is present in the fiber-reinforced plastic intermediate material 10 (step S4). When determining that the defect is present in the fiber-reinforced plastic intermediate material 10 (step S4, Defect is found), the user repairs the fiber-reinforced plastic intermediate material 10 (step S5).

When it is determined that no defect is caused in the fiber-reinforced plastic intermediate material 10 (step S4, No defect is found) or after the step S5 is performed, the user forms fiber-reinforced plastic from the fiber-reinforced plastic intermediate material 10 by heating the resin to a high temperature so that the resin is hardened (step S6). The user checks whether any defect is present in the fiber-reinforced plastic (step S7), and completes the fiber-reinforced plastic when no defect is found in the fiber-reinforced plastic.

Figure 5:
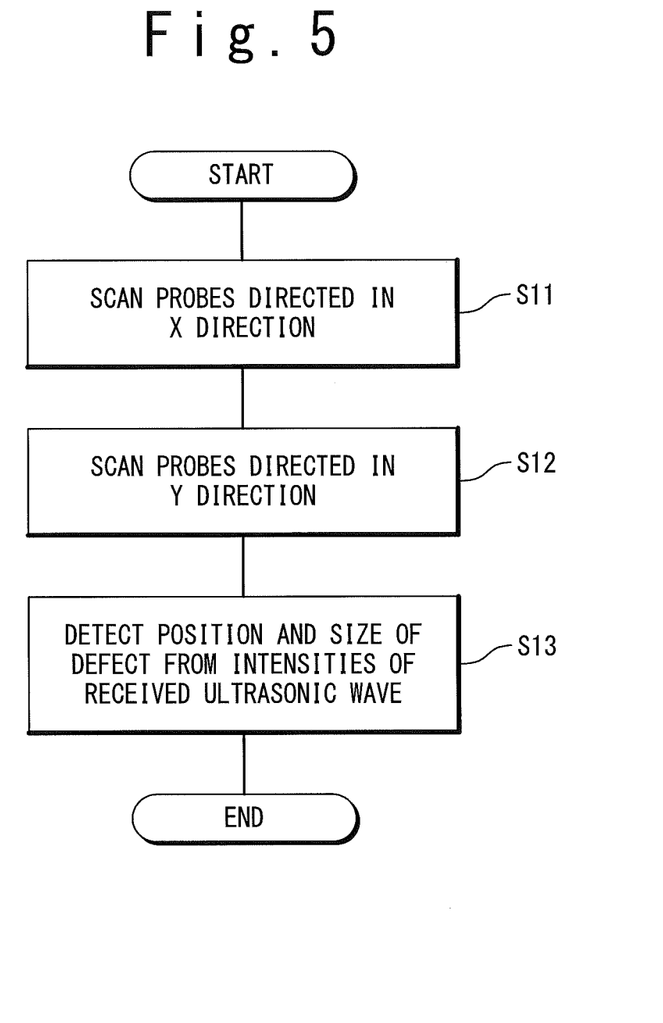
FIG. 5 is a flow chart showing a nondestructive inspection method.

FIG. 5 shows the nondestructive inspection method performed in the step S4. The nondestructive inspection method is performed by the nondestructive inspection apparatus 14. The control unit 17 of the nondestructive inspection apparatus 14 firstly drives the third driving unit 38 so that the transmission-side probe 15 and the reception-side probe 16 are arranged to direct in the x-axis direction. The control unit 17 controls the transmission-side probe 15 and the reception-side probe 16 to be scanned in a state that the transmission-side probe 15 and the reception-side probe 16 are directed in the x-axis direction. That is to say, a part surrounded by the sidewall portion 8 corresponding to the plate portion 7 is divided into a plurality of regions in a matrix pattern. The control unit 17 controls the first driving unit 36 and the second driving unit 37 so that the transmission-side probe 15 is directed toward each of the regions in order. The control unit 17 emits the ultrasonic wave 21 by using the transmission-side probe 15 each time the transmission-side probe 15 is directed toward each of the regions. At this time, the ultrasonic wave 21 is propagated to the plate portion 7 of the mold 2 through the fiber-reinforced plastic intermediate material 10 in the mold 2. The plate portion 7 generates the Lamb wave 23 at the point 22 to which the ultrasonic wave 21 is propagated, and the Lamb wave 23 is propagated to an optional point of the plate portion 7, and an ultrasonic wave is emitted from that point 24. The reception-side probe 16 measures intensity of the ultrasonic wave 25 emitted from the point 24 away from the point 22 by a given distance in the x-axis direction. The control unit 17 collects the intensities of the ultrasonic wave 25 from the reception-side probe 16 (step S11).

Next, the control unit 17 controls the third driving unit 38 so that the transmission-side probe 15 and the reception-side probe 16 are directed in the y-axis direction. The control unit 17 controls the transmission-side probe 15 and the reception-side probe 16 to be scanned in a state that the transmission-side probe 15 and the reception-side probe 16 are directed in the y-axis direction. The control unit 17 emits the ultrasonic wave 21 by using the transmission-side probe 15 each time the transmission side probe 15 is directed toward each of the regions of the plate portion 7. The reception-side probe 16 measures intensity of the ultrasonic wave 25 emitted from the point 24 away from the point 22 by a given distance in the y-axis direction. The control unit 17 collects the intensities of the ultrasonic wave 25 from the reception-side probe 16 (step S12).

The control unit 17 determines whether any defect is caused in the fiber-reinforced plastic intermediate material 10, based on the intensities of the ultrasonic wave 25 collected in the step S11 and the intensities of the ultrasonic wave 25 collected in the step S12. The defect is exemplified by a void and failure of impregnation. The void means formation of an air bubble in the resin portion 19 of the fiber-reinforced plastic intermediate material 10 due to a hole formed in the bag film 3, for example. The failure of impregnation means a state in which carbon fiber remains bared due to insufficiency of resin impregnation. When it is determined that the defect is caused in the fiber-reinforced plastic intermediate material 10, the control unit 17 calculates a position, type, and size of the defect based on the collected intensities of the ultrasonic wave 25 (step S13). The control unit 17 further displays the calculated position, type, and size of the defect on the display so that the user can recognize the calculated position, type, and size of the defect.

According to the nondestructive inspection method, it is not necessary for the transmission-side probe 15 and the reception-side probe 16 to come into contact with the bag film 3, to provide a liquid contact medium between the transmission-side probe 15 and the bag film 3, and to provide any liquid contact medium between the reception-side probe 16 and the bag film 3. For this reason, the nondestructive inspection apparatus 14 does not contaminate the furnace where the composite material curing tool 1 is placed, with the contact medium, making it possible to prevent contamination inside the furnace.

In the nondestructive inspection method, a position and size of a defect caused in the fiber-reinforced plastic intermediate material 10 can be calculated, since the transmission-side probe 15 and the reception-side probe 16 are scanned. Intensity of the ultrasonic wave 25 reflects a thickness of the resin portion 19 at a portion where the ultrasonic wave 21 is propagated in the fiber-reinforced plastic intermediate material 10, or a thickness of the resin portion 19 at a portion where the ultrasonic wave 25 is propagated in the fiber-reinforced plastic intermediate material 10. In general, it is not possible to determine which of the two thicknesses is reflected. According to the nondestructive inspection method, it is possible to calculate a position and size of a defect caused in the fiber-reinforced plastic intermediate material 10 more in detail since the inspections are performed more than one time by changing a direction in which the transmission-side probe 15 and the reception-side probe 16 are directed.

In general, repair of fiber-reinforced plastic after a resin portion is hardened lowers the strength of a repaired portion. According to the composite material manufacturing method, it is possible to repair a defect without lowering the strength of a finished product, since the defect of the fiber-reinforced plastic intermediate material 10 can be found before the resin portion 19 is hardened by the nondestructive inspection method. It should be noted that the step S5 can be replaced by operation to discard the fiber-reinforced plastic intermediate material 10. At this time, it is possible to prevent unnecessary performance of hardening which is the next process of resin injection in the step S3.

The nondestructive inspection method can further be applied to other methods handling a fluid. The methods are exemplified by manufacturing of concrete. According to a concrete manufacturing method to which the nondestructive inspection method is applied, a defect (void) caused in concrete can be found before the concrete is cured, which is preferable.

It should be noted that the plate portion 7 of the mold 2 can be replaced by another plate which is not flat. According to the composite material manufacturing method using the mold, it is possible to mold fiber-reinforced plastic having a curved surface, which is not flat.

It should be noted that the mold 2 can be replaced by another mold further having a Lamb-wave propagation plate on a side opposite to the sidewall portions 8 or the plate portion 7. Such a mold is used in the same way as the mold 2 in the above embodiment. That is to say, the Lamb-wave propagation plate receives an ultrasonic wave propagated from the transmission-side probe 15 through the fiber-reinforced plastic intermediate material and a plate portion of the mold, generates a Lamb wave at a point where the ultrasonic wave is propagated, propagates the Lamb wave to any point of the Lamb-wave propagation plate, and emits an ultrasonic wave from the point. At this time, the reception-side probe 16 measures intensity of the ultrasonic wave emitted from the Lamb-wave propagation plate and propagated through the plate portion of the mold and the fiber-reinforced plastic intermediate material. The nondestructive inspection method using such a mold can have the same effect as the nondestructive inspection method according to the above embodiment.

The invention claimed is:

1. A nondestructive inspection apparatus comprising:
a plate for supporting a test-target fluid;
a transmission-side probe disposed on one side of the plate and arranged such that the test-target fluid will be between the plate and the transmission-side probe, the transmission-side probe being configured to emit a first ultrasonic wave toward the test fluid;
a reception-side probe disposed on the one side of the plate and arranged such that the test-target fluid will be between the plate and the reception-side probe,
wherein the plate is configured to generate a Lamb wave based on the first ultrasonic wave propagated through the test-target fluid and propagate the Lamb wave to another portion of the plate, and to generate a second ultrasonic wave based on the Lamb wave and propagate the second ultrasonic wave to the test-target fluid,
the reception-side probe is configured and arranged to receive the second ultrasonic wave propagated through the test-target fluid and measure intensity of the second ultrasonic wave, and
the transmission-side probe and the reception-side probe are not in contact with any liquid including the test-target fluid.

2. The nondestructive inspection apparatus of claim 1, wherein the plate is formed as part of a mold where the test-target fluid is injected.

3. The nondestructive inspection apparatus of claim 2, further comprising:
a fixing member configured to fix the reception-side probe to the transmission-side probe.

4. The nondestructive inspection apparatus of claim 3, further comprising:
a first driving unit configured to drive the transmission-side probe and the reception-side probe.

5. The nondestructive inspection apparatus of claim 4, further comprising:
a second driving unit configured to change a direction of the reception-side probe with respect to the transmission-side probe.

6. The nondestructive inspection apparatus of claim 2, wherein the test-target fluid is a resin which is curable to a hardened state, and
wherein the apparatus further comprises a control unit configured to detect timing at which the test-target fluid is cured to the hardened state, based on intensities of the second ultrasonic wave.

7. A nondestructive inspection apparatus comprising:
a plate for supporting a test-target fluid;
a transmission-side probe disposed on one side of the plate and arranged such that the test-target fluid will be between the plate and the transmission-side probe, the transmission-side probe being configured to emit a first ultrasonic wave toward the test fluid;
a reception-side probe disposed on the one side of the plate and arranged such that the test-target fluid will be between the plate and the reception-side probe;
a first driving unit configured to drive the transmission-side probe and the reception-side probe;
a second driving unit configured to change a direction of the reception-side probe with respect to the transmission-side probe; and
a control unit,
wherein the plate is configured to generate a Lamb wave based on the first ultrasonic wave propagated through the test-target fluid and propagate the Lamb wave to another portion of the plate, and to generate a second ultrasonic wave based on the Lamb wave and propagate the second ultrasonic wave to the test-target fluid,
the reception-side probe is configured and arranged to receive the second ultrasonic wave propagated through the test-target fluid and measure intensity of the second ultrasonic wave, and
the control unit comprises:
a scanning section configured to scan the transmission-side probe and the reception-side probe using the first driving unit after directing the transmission-side probe and the reception-side probe in a first direction with the second driving unit, and scan the transmission-side probe and the reception-side probe using the first driving unit after directing the transmission-side probe and the reception-side probe in a second direction different from the first direction with the second driving unit;
a collecting section configured to collect intensities of the second ultrasonic wave from the reception-side probe while the transmission-side probe and the reception-side probe are scanned; and
a defect detecting section configured to detect a position where the test-target fluid is not appropriate, based on the intensities.

8. A nondestructive inspection method comprising:
emitting a first ultrasonic wave toward a test-target fluid from a transmission-side probe disposed on one side of the test-target fluid such that the first ultrasonic wave is propagated to a plate through the test-target fluid;
generating a Lamb wave in the plate based on the first ultrasonic wave to propagate the Lamb wave to another portion of the plate;
generating a second ultrasonic wave based on the Lamb wave to emit the second ultrasonic wave from the plate into the test-target fluid;
measuring intensities of the second ultrasonic wave propagated through the test-target fluid using a reception-side prove disposed on the one side of the test-target fluid; and
inspecting a defect portion in the test-target fluid based on the intensities.

9. The nondestructive inspection method of claim 8, further comprising scanning the transmission-side probe and the reception-side probe.

10. The nondestructive inspection method of claim 9, wherein the scanning comprises:
scanning the transmission-side probe and the reception-side probe in a state that the transmission-side probe and the reception-side probe are directed in a first direction; and
scanning the transmission-side probe and the reception-side probe in a state that the transmission-side probe and the reception-side probe are directed in a second direction different from the first direction.

11. A composite material manufacturing method comprising:
performing a nondestructive inspection method which includes
(i) emitting a first ultrasonic wave toward a test-target fluid from a transmission-side probe disposed on one side of the test-target fluid such that the first ultrasonic wave is propagated to a plate through the test-target fluid,
(ii) generating a Lamb wave in the plate based on the first ultrasonic wave to propagate the Lamb wave to another portion of the plate,
(iii) generating a second ultrasonic wave based on the Lamb wave to emit the second ultrasonic wave from the plate into the test-target fluid,
(iv) measuring intensities of the second ultrasonic wave propagated through the test-target fluid using a reception-side prove disposed on the one side of the test-target fluid, and
(v) inspecting a defect portion in the test-target fluid based on the intensities;
repairing the defect portion; and
after the repairing, performing a next process.

12. The composite material manufacturing method of claim 11, wherein the test-target fluid is a resin, and
wherein the next process includes hardening the resin.

13. The composite material manufacturing method of claim 11, further comprising scanning the transmission-side probe and the reception-side probe.

14. The composite material manufacturing method of claim 11, wherein the scanning comprises:
scanning the transmission-side probe and the reception-side probe in a state that the transmission-side probe and the reception-side probe are directed in a first direction; and
scanning the transmission-side probe and the reception-side probe in a state that the transmission-side probe and the reception-side probe are directed in a second direction different from the first direction.

15. A nondestructive inspection apparatus comprising:
a plate for supporting a test-target fluid;
a transmission-side probe disposed on one side of the plate and arranged such that the test-target fluid will be between the plate and the transmission-side probe, the transmission-side probe being configured to emit a first ultrasonic wave toward the test fluid;
a reception-side probe disposed on the one side of the plate and arranged such that the test-target fluid will be between the plate and the reception-side probe; and
a control unit,
wherein the plate is configured to generate a Lamb wave based on the first ultrasonic wave propagated through the test-target fluid and propagate the Lamb wave to another portion of the plate, and to generate a second ultrasonic wave based on the Lamb wave and propagate the second ultrasonic wave to the test-target fluid,
wherein the reception-side probe is configured and arranged to receive the second ultrasonic wave propagated through the test-target fluid and measure intensity of the second ultrasonic wave, and
wherein the control unit is configured to collect information of the measured intensity of the second ultrasonic wave from the reception-side probe,
the control unit is configured to determine whether or not any defect is present in the test-target fluid based on the measured intensity or display information based on the measured intensity on a display.

16. The nondestructive inspection apparatus of claim 15, wherein the plate is formed as part of a mold where the test-target fluid is injected.

17. The nondestructive inspection apparatus of claim 16, further comprising:
a fixing member configured to fix the reception-side probe to the transmission-side probe.

18. The nondestructive inspection apparatus of claim 17, further comprising:
a first driving unit configured to drive the transmission-side probe and the reception-side probe.

19. The nondestructive inspection apparatus of claim 18, further comprising:
A second driving unit configured to change a direction of the reception-side probe with respect to the transmission-side probe.

* * * * *